(12) United States Patent
Cogley

(10) Patent No.: US 10,492,992 B1
(45) Date of Patent: Dec. 3, 2019

(54) OINTMENT APPLICATION SYSTEM

(71) Applicant: Thomas Paul Cogley, Pinellas Park, FL (US)

(72) Inventor: Thomas Paul Cogley, Pinellas Park, FL (US)

(\*) Notice: Subject to any disclaimer, the term of this patent is extended or adjusted under 35 U.S.C. 154(b) by 427 days.

(21) Appl. No.: 15/405,809

(22) Filed: Jan. 13, 2017

Related U.S. Application Data

(60) Provisional application No. 62/279,333, filed on Jan. 15, 2016.

(51) Int. Cl.
| | |
|---|---|
| *A61M 35/00* | (2006.01) |
| *A61J 1/20* | (2006.01) |
| *A61K 9/06* | (2006.01) |
| *A61K 31/7048* | (2006.01) |
| *A61K 31/7036* | (2006.01) |
| *A61K 38/12* | (2006.01) |
| *A61K 31/58* | (2006.01) |
| *A61K 47/34* | (2017.01) |
| *A61M 31/00* | (2006.01) |
| *A61M 39/24* | (2006.01) |

(52) U.S. Cl.
CPC ............... *A61J 1/2093* (2013.01); *A61K 9/06* (2013.01); *A61K 31/58* (2013.01); *A61K 31/7036* (2013.01); *A61K 31/7048* (2013.01); *A61K 38/12* (2013.01); *A61K 47/34* (2013.01); *A61M 31/005* (2013.01); *A61M 35/003* (2013.01); *A61M 39/24* (2013.01); *A61M 2250/00* (2013.01)

(58) Field of Classification Search
CPC .. A61J 1/2093; A61M 31/005; A61M 35/003; A61M 39/24; A61M 2250/00; A61K 9/06; A61K 31/58; A61K 31/7036; A61K 31/7048; A61K 38/12; A61K 47/34
USPC .......................................................... 604/310
See application file for complete search history.

(56) References Cited

U.S. PATENT DOCUMENTS

| | | | | |
|---|---|---|---|---|
| 2,112,160 | A * | 3/1938 | Johnson ................. | A61M 5/19 24/546 |
| 6,543,954 | B2 * | 4/2003 | Owings .................. | A45D 34/04 401/185 |
| 2007/0287966 | A1 * | 12/2007 | Keeley .................... | A61M 1/28 604/246 |
| 2008/0214460 | A1 * | 9/2008 | Neuberger ............. | A61L 27/50 514/20.1 |
| 2011/0268490 | A1 * | 11/2011 | Acierto .................. | A45D 34/04 401/37 |
| 2012/0215205 | A1 * | 8/2012 | Alvey ................... | A61J 1/2093 604/516 |

(Continued)

OTHER PUBLICATIONS

Animax Ointment for Animal Use. (Jul. 12, 2007). Retrieved May 10, 2019, from https://www.drugs.com/vet/animax-ointment.html (Year: 2007).*

*Primary Examiner* — Andrew J Mensh

(57) ABSTRACT

An ointment squeeze ball has an exit orifice for dispensing ointment. A colorant squeeze ball has an exit orifice for dispensing colorant. A mixing tube has an input end, an exit applicator tip, and an elongated passageway with helical mixing vanes. A central component in a Y-shaped configuration with a central passageway removably couples the ointment squeeze ball and the mixing tube. The central component has a lateral leg with a lateral passageway removably coupling the colorant squeeze ball and an intermediate region of the central passageway.

1 Claim, 3 Drawing Sheets

(56) References Cited

U.S. PATENT DOCUMENTS

2017/0073465 A1\* 3/2017 Smith .................. A61K 9/0014
2017/0232148 A1\* 8/2017 Nguyen .................. A61L 27/26
                                                                                                    514/180

\* cited by examiner

OINTMENT APPLICATION SYSTEM

BACKGROUND OF THE INVENTION

Field of the Invention

The present invention relates to an ointment application system and more particularly pertains to supporting an ointment and a colorant, mixing the ointment and colorant, applying the mixed ointment and colorant to wounds, ears, or the area around eyes of pets to be treated. The supporting, mixing and applying are done in an accurate, safe, sanitary, convenient, and economical manner.

Description of the Prior Art

The use of ointment application systems of known designs and configurations is known in the prior art. More specifically, ointment application systems of known designs and configurations previously devised and utilized for the purpose of applying ointment to a wound are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, they do not describe an ointment application system that allows supporting an ointment and a colorant, mixing the ointment and colorant, applying the mixed ointment and colorant to wounds, ears, or the area around eyes of pets to be treated. The supporting, mixing and applying are done in an accurate, safe, sanitary, convenient, and economical manner.

In this respect, the ointment application system according to the present invention substantially departs from the conventional concepts and designs of the prior art, and in doing so provides an apparatus primarily developed for the purpose of supporting an ointment and a colorant, mixing the ointment and colorant, applying the mixed ointment and colorant to wounds, ears, or the area around eyes of pets to be treated. The supporting, mixing and applying are done in an accurate, safe, sanitary, convenient, and economical manner.

Therefore, it can be appreciated that there exists a continuing need for a new and improved ointment application system which can be used for supporting an ointment and a colorant, mixing the ointment and colorant, applying the mixed ointment and colorant to wounds, ears, or the area around eyes of pets to be treated. The supporting, mixing and applying are done in an accurate, safe, sanitary, convenient, and economical manner. In this regard, the present invention substantially fulfills this need.

SUMMARY OF THE INVENTION

In view of the foregoing disadvantages inherent in the known types of ointment application systems of known designs and configurations now present in the prior art, the present invention provides an improved ointment application system. As such, the general purpose of the present invention, which will be described subsequently in greater detail, is to provide a new and improved ointment application system and method which has all the advantages of the prior art and none of the disadvantages.

To attain this, the present invention essentially comprises an ointment application system. In a broad context, an ointment squeeze ball has an exit orifice for dispensing ointment. A colorant squeeze ball has an exit orifice for dispensing colorant. A mixing tube has an input end, an exit applicator tip, and an elongated passageway with helical mixing vanes. A central component in a Y-shaped configuration with a central passageway removably couples the ointment squeeze ball and the mixing tube. The central component has a lateral leg with a lateral passageway removably coupling the colorant squeeze ball and an intermediate region of the central passageway.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved ointment application system which has all of the advantages of the prior art ointment application systems of known designs and configurations and none of the disadvantages.

It is another object of the present invention to provide a new and improved ointment application system which may be easily and efficiently manufactured and marketed.

It is further object of the present invention to provide a new and improved ointment application system which is of durable and reliable constructions.

An even further object of the present invention is to provide a new and improved ointment application system which is susceptible of a low cost of manufacture with regard to both materials and labor, and which accordingly is then susceptible of low prices of sale to the consuming public, thereby making such ointment application system economically available to the buying public.

Lastly, another object of the present invention is to provide an ointment application system for supporting an ointment and a colorant, mixing the ointment and colorant, applying the mixed ointment and colorant to wounds, ears, the area around eyes of pets to be treated. The supporting, mixing and applying are done in an accurate, safe, sanitary, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
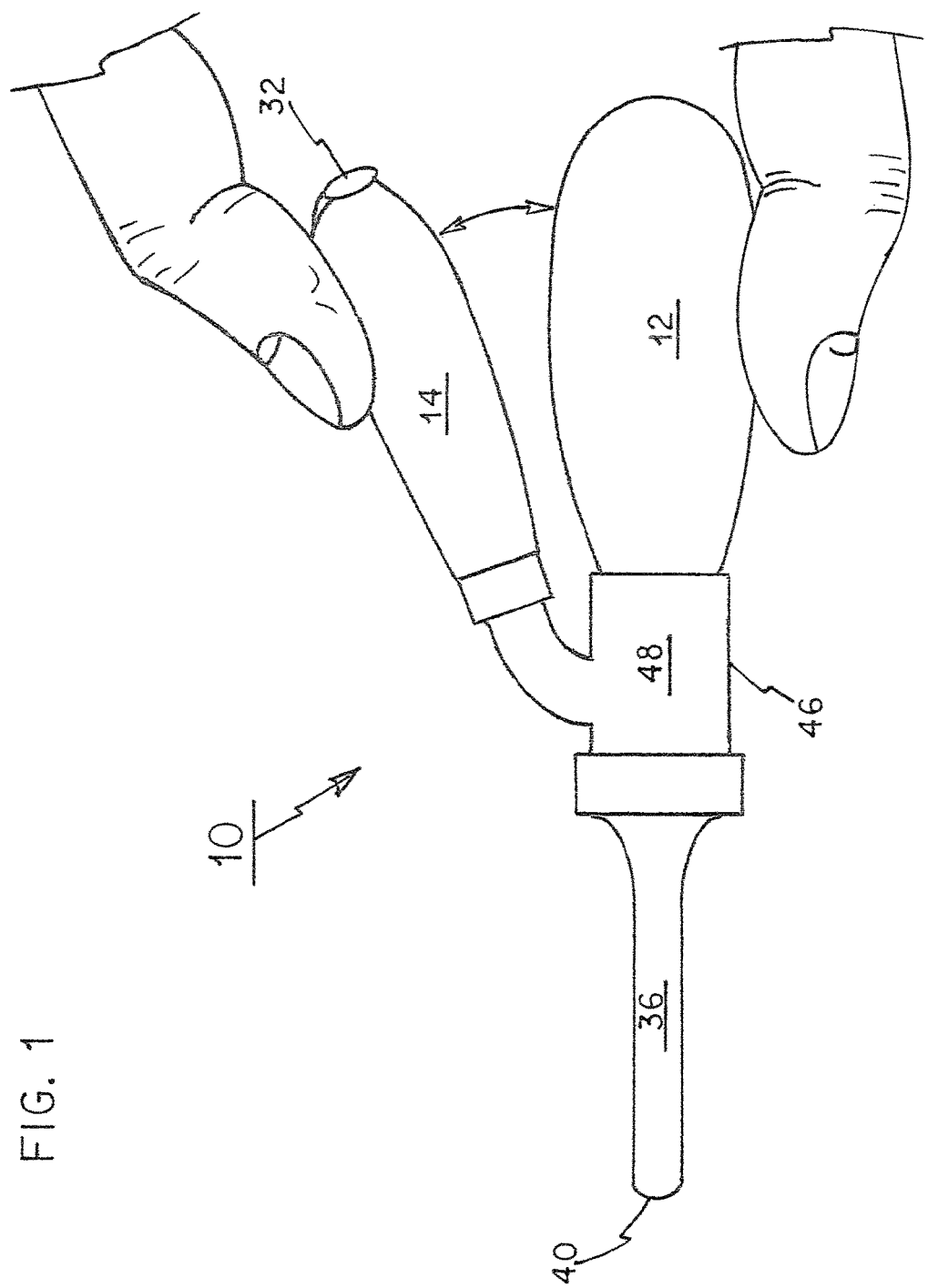
FIG. 1 is a side elevational view of an ointment application system constructed in accordance with the principles of the present invention, the system being shown in the hand of a user squeezing together an ointment squeeze ball and a colorant squeeze to dispense together an ointment and a colorant, the system being particularly useful in treating wounds, ears, and the area around eyes of pets, such as cats and dogs.
Figure 2:
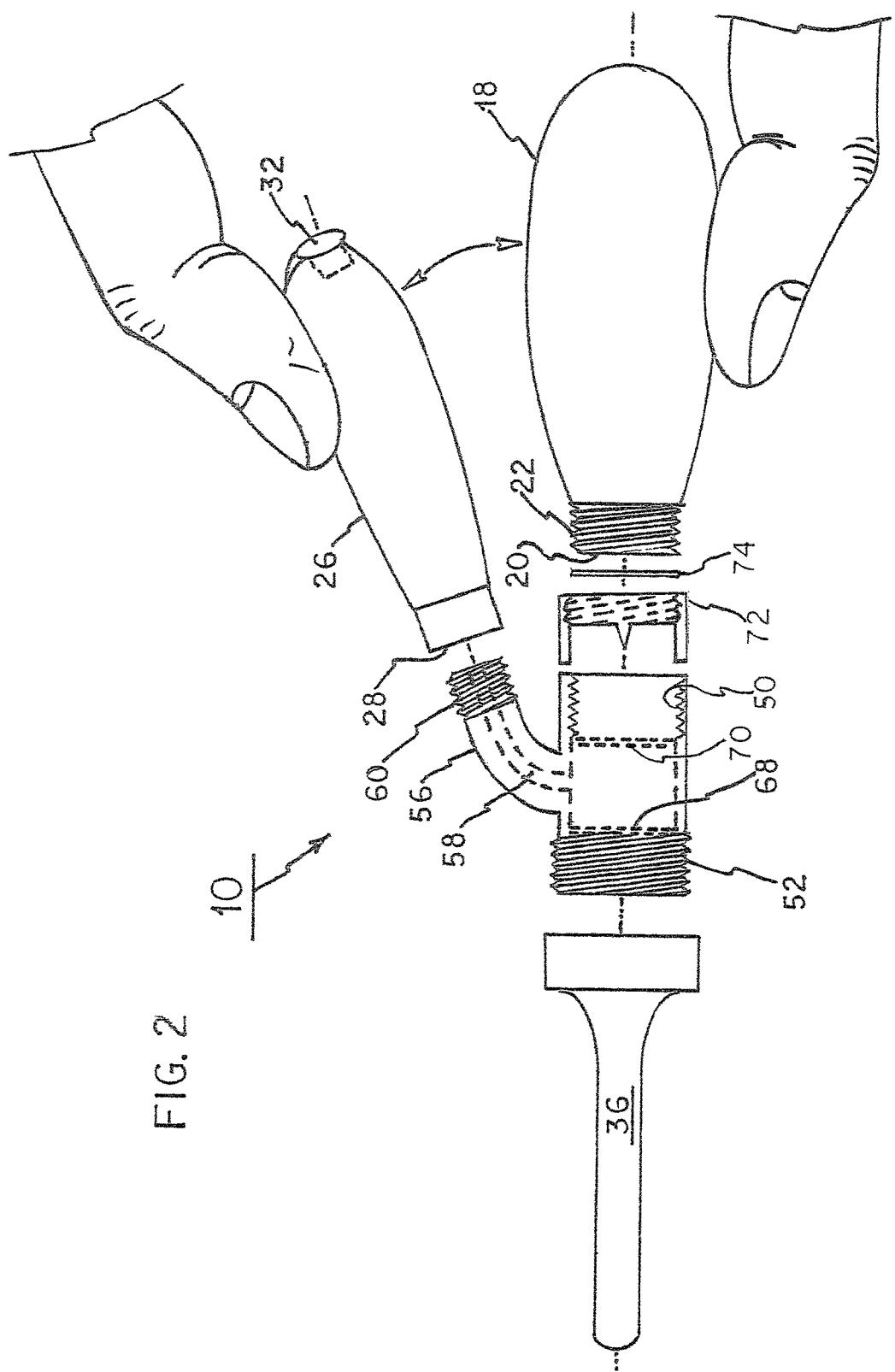
FIG. 2 is an exploded side elevational view of the system of FIG. 1.
Figure 3:
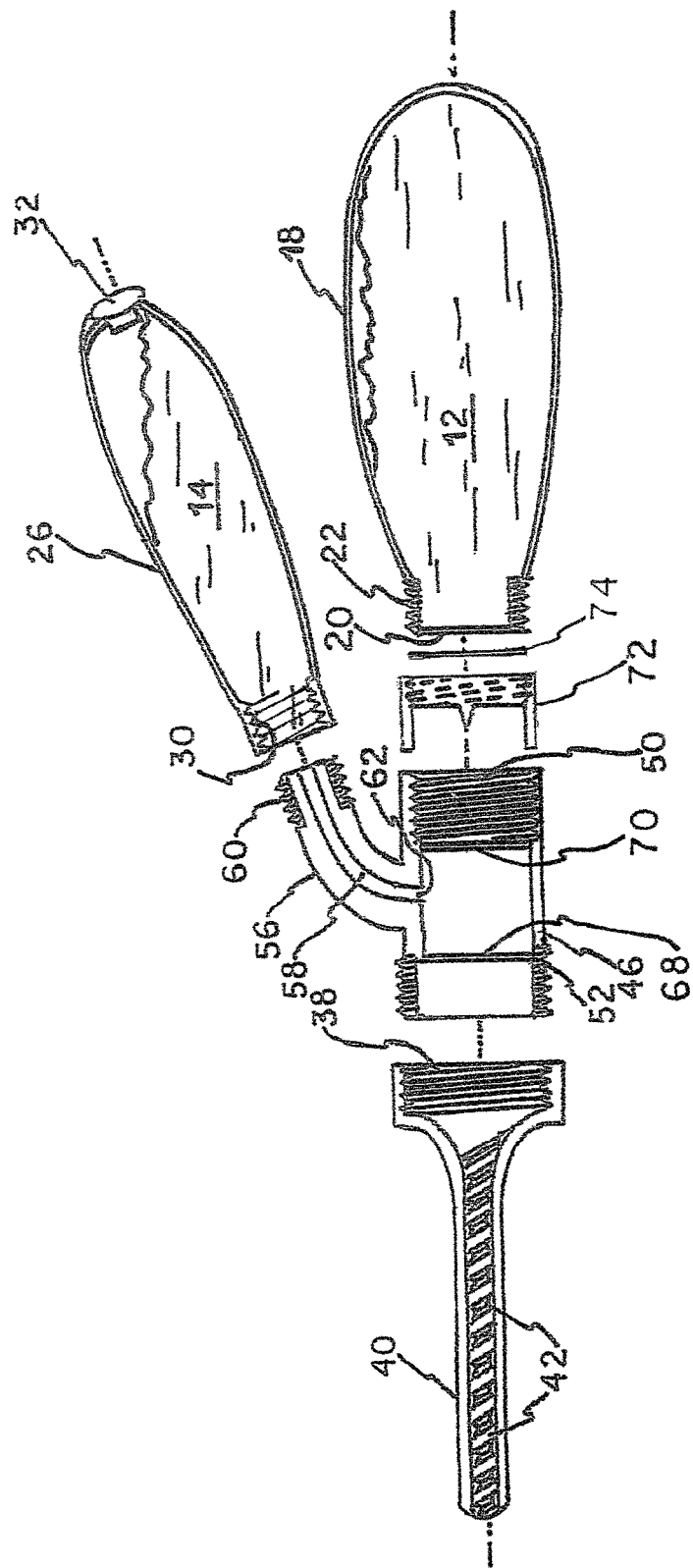
FIG. 3 is a cross-sectional view taken axially through the system of FIG. 1.

With reference now to the drawings, and in particular to FIG. 1 thereof, the preferred embodiment of the new and improved ointment application system embodying the principles and concepts of the present invention and generally designated by the reference numeral 10 will be described.

The present invention, the ointment application system 10 is comprised of a plurality of components. Such components in their broadest context include an ointment squeeze ball, a colorant squeeze ball, a mixing tube, and a central component. Such components are individually configured and correlated with respect to each other so as to attain the desired objective.

From a specific viewpoint, the invention is an ointment application system 10 for supporting an ointment 12 and a colorant 14, for mixing the supported ointment and colorant, and for applying the mixed ointment and colorant to wounds, ears, the area around eyes of pets to be treated to be treated. The supporting and the mixing and the applying are done in an accurate, safe, sanitary, convenient, and economical manner.

First provided is an ointment squeeze ball 18 with a quantity of ointment 12. The ointment squeeze ball has an exit orifice 20 with male screw threads 22. The ointment squeeze ball is adapted to be squeezed by a user for dispensing ointment through the ointment exit orifice. For each milliliter, the ointment comprises 100,000 units of nystatin, 2.5 milligrams neomycin sulfate equivalent to neomycin base, 2,500 units thiostrepton, and 1.0 milligram triamcinolone acetonide in a polyurethane and mineral gel base.

Next provided is a colorant squeeze ball 26 with a quantity of colorant 14. The colorant squeeze ball has a colorant exit orifice 28 with female screw threads 30. The colorant squeeze ball has an opening with a plug 32 for filling the colorant squeeze ball with colorant. The colorant squeeze ball is adapted to be squeezed by a user for dispensing colorant through the colorant exit orifice. The colorant is chosen from the class of colorants consisting of alumina, beta-carotene, caramel, and talc, the colorant being a fluorescent fluid which is black light responsive whereby the user may readily detect colorant. In this manner, the user may readily detect colorant in the admixture.

A mixing tube 36 is next provided. The mixing tube has a mixing tube input end with female screw threads 38. The mixing tube has an output end with an exit applicator tip 40. The mixing tube has an elongated passageway with helical vanes 42 for mixing ointment and colorant passing there through.

Next provided is a central component 46 in a Y-shaped configuration. The central component has a linear central passageway 48. The linear central passageway is cylindrical with female screw threads 50 removably receiving the male screw threads of the ointment squeeze ball. The central component has male screw thread 52 removably receiving the female screw threads of the mixing tube.

The Y-shaped connector has a lateral leg 56 with a lateral passageway 58. The lateral passageway 58 has male screw threads 60 removably receiving the female screw threads of the colorant squeeze ball. An output end 62 of the lateral leg is at an intermediate region of the central passageway.

Next provided is a one way flapper valve 68. The one way flapper valve is in the linear central passageway adjacent to the mixing tube. The one way flapper valve precludes reverse flow of ointment and colorant.

A second one way flapper valve 70 is provided. The second one way flapper valve is in the linear central passageway adjacent to female threads 50.

Lastly, a seal 72 is provided. The seal is removably positioned in the ointment squeeze ball. The seal is to be removed prior to coupling the ointment squeeze ball to the central component. The seal has a first end threadedly coupled to the ointment squeeze ball. The seal has a second end with an axial needle for piercing a covering membrane 74 in the ointment squeeze ball.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ointment application system (10) for supporting an ointment (12) and a colorant (14), for mixing the supported ointment and colorant, and for applying the mixed ointment and colorant to wounds, ears, and the area around eyes of pets to be treated, the supporting and the mixing and the applying being done in an accurate, safe, sanitary, convenient, and economical manner, the system comprising, in combination:

an ointment squeeze ball (18) with a quantity of ointment (12), the ointment squeeze ball having an exit orifice (20) with male screw threads (22), the ointment squeeze ball adapted to be squeezed by a user for dispensing ointment through the ointment exit orifice, wherein for each milliliter, the ointment comprises 100,000 units of nystatin, 2.5 milligrams neomycin sulfate equivalent to neomycin base, 2,500 units thiostrepton, and 1.0 milligrams triamcinolone acetonide in a polyurethane and mineral gel base;

a colorant squeeze ball (26) with a quantity of colorant (14), the colorant squeeze ball having a colorant exit orifice (28) with female screw threads (30), the colorant squeeze ball having an opening with a plug (32) for filling the colorant squeeze ball with colorant, the colorant squeeze ball adapted to be squeezed by a user for dispensing colorant through the colorant exit orifice, the colorant being chosen from the class consisting of alumina, beta-carotene, caramel, and talc, the colorant being a fluorescent fluid which is black light responsive whereby the user may readily detect colorant;

a mixing tube (36) having a mixing tube input end with female screw threads (38), the mixing tube having an output end with an exit applicator tip (40), the mixing tube having an elongated passageway with helical vanes (42) for mixing ointment and colorant passing there through;

a central component (46) in a Y-shaped configuration with a linear central passageway (48), the linear central passageway being cylindrical with female screw threads (50) removably receiving the male screw threads of the ointment squeeze ball, the central component having male screw thread (52) removably receiving the female screw threads of the mixing tube;

the Y-shaped connector having a lateral leg (56) having a lateral passageway, the lateral passageway having male screw threads (60) removably receiving the female screw threads of the colorant squeeze ball, and with an output end (62) of the lateral leg at an intermediate region of the central passageway;

a one way flapper valve (60) in the linear central passageway adjacent to the mixing tube to preclude reverse flow of ointment and colorant;

a second one way flapper valve (70) in the linear central passageway adjacent to the female threads (50) of the central component to preclude reverse flow of ointment and colorant; and a seal (72) removably positioned in the ointment squeeze ball to be removed prior to coupling the ointment squeeze ball to the central component, the seal having a first end threadedly coupled to the ointment squeeze ball, the seal having a second end with an axial needle for piercing a covering membrane (74) in the ointment squeeze ball, the second end also including a cylindrical periphery.

\* \* \* \* \*